United States Patent [19]

Czarnecki

[11] Patent Number: 5,055,264

[45] Date of Patent: Oct. 8, 1991

[54] APPARATUS FOR DIRECTING THE FLOW OF CONDENSABLE MATTER

[75] Inventor: Jerzy P. Czarnecki, La Habra, Calif.

[73] Assignee: Cahn Instruments, Inc., Cerritos, Calif.

[21] Appl. No.: 268,784

[22] Filed: Nov. 8, 1988

[51] Int. Cl.$^5$ .................... G01N 31/12; G01N 25/00
[52] U.S. Cl. ............................ 422/80; 422/78; 177/212; 374/14
[58] Field of Search ............ 422/78, 80; 177/212; 374/14

[56] References Cited

U.S. PATENT DOCUMENTS

| | | | |
|---|---|---|---|
| 3,055,206 | 9/1962 | Watson et al. | 374/14 |
| 3,554,001 | 1/1971 | Norem | 374/14 |
| 3,717,210 | 2/1973 | Sieswerda | 177/212 |
| 3,902,354 | 9/1975 | Harlan et al. | 374/14 |
| 4,087,249 | 5/1978 | Okumoto et al. | 422/78 |
| 4,606,649 | 8/1986 | Mikhail | 374/14 |
| 4,625,819 | 12/1986 | O'Neill | 177/212 |
| 4,817,745 | 4/1989 | Beshoory | 177/212 |
| 4,824,790 | 8/1989 | Carangelo et al. | 422/80 |
| 4,838,706 | 6/1989 | Coey et al. | 73/19.01 |

FOREIGN PATENT DOCUMENTS

| | | | |
|---|---|---|---|
| 2534258 | 2/1977 | Fed. Rep. of Germany | 422/78 |
| 0377676 | 4/1973 | U.S.S.R. | 374/14 |
| 1236286 | 6/1986 | U.S.S.R. | 422/80 |

OTHER PUBLICATIONS

Setarm Scientific Instruments brochure, p. 4, date unknown.
Advanced Composites, *Thermal Analysis-a Quick Fix on Product Performance*, pp. 38, 39, 42 and 44, Sep./Oct. 1988.

*Primary Examiner*—Robert J. Warden
*Assistant Examiner*—Theresa A. Trembley
*Attorney, Agent, or Firm*—Merchant, Gould, Smith, Edell, Welter & Schmidt

[57] ABSTRACT

An apparatus for controlling the flows of products of decomposition in a thermogravimetric procedure such that condensation on the support for a sample and on the chamber is minimized. A mixing chamber is established about a portion of the sample support that is open to the region of the sample such that products of decomposition can enter within the hot zone about the sample. A purge gas is fed into the interior of the mixing chamber, also the hot zone, but spaced apart from the end closest to the sample. The gases commingle within the mixing chamber and are extracted from the thermogravimetric chamber via outlets in a cooler region.

11 Claims, 5 Drawing Sheets

5,055,264

APPARATUS FOR DIRECTING THE FLOW OF CONDENSABLE MATTER

BACKGROUND OF THE INVENTION

This invention relates to systems for measuring changes of mass during a dynamic process, and more particularly to systems and devices for directing the flow of condensable gases so that measurements of mass can be precisely obtained.

Modern precision mass measuring systems, such as electromagnetic balances and similar devices, are capable of such precise measurements that the change in mass of a small sample subject to a decomposition reaction can be precisely monitored as changes occur, thus revealing needed information about the mass that is under examination. This technique is used with modern thermogravimetric instruments that are widely employed in industry and scientific laboratories. In such instruments, a test quantity on a sample holder is held in a furnace and coupled to a precision balance. The sample holder is typically suspended within a thermogravimetric chamber on a thin hang-down wire, the chamber passing through the furnace, which heats the sample to a fixed or changing temperature level. The hang-down wire is coupled at its outer, cool, end to the balance, which is protected in a chamber by a purge gas atmosphere. The sample is usually thermally decomposed under the influence of temperature, with or without a reactive gas, with the dynamic variations in mass being recorded for subsequent analysis. Obviously, what is desired is to obtain a reading which represents changes in mass of the sample only, but this has heretofore been very difficult to achieve because of the difficulty of keeping the flowing gas, after decomposition, away from the cooler portions of the hang-down wire and associated structure. In a typical case, products of decomposition are impelled, along with the purge gas, toward an outlet from the furnace. The gas tends to move upwardly, toward and along the hang-down wire, and a cooler region is reached in which these products condense on the hang-down wire, introducing an increasing error in the mass reading as the reaction proceeds. Condensation may also occur on the chamber walls, rendering them opaque and requiring frequent cleaning or replacement.

Because of the high resolution of the measurements involved, the condensation of matter on the hang-down wire cannot be ignored, but must be compensated for imperfectly by calculation or subsequent independent measurement. It is not feasible to expand the hot zone so as to limit condensation problems because a cooler region must inevitably be encountered and the sample support mechanism and thermogravimetric chamber should not be excessively large. Also, flows and relationships should be kept as invariant as possible. For example, the gas composition in the region of the sample can vary if the effluent, reactant and purge gases are not maintained in the proper relationship. The reactant also should reach the sample at substantially the same temperature and with the same concentration at all times, which is not the case if the flows vary with time. Mixing of reactant with purge gas at the sample must be eliminated to the fullest extent possible in order to maintain constancy of the gas composition. Also, the measurements being made are so sensitive that the differential pressure exerted by gas flows affect the readings and thus must be held constant.

SUMMARY OF THE INVENTION

Devices and methods in accordance with the invention provide positive control of gases flowing in the region of a sample in a high temperature thermogravimetric chamber. Opposite flows of purge and reactant gases are arranged so that the reaction is constant and condensation of matter on the support mechanism for a sample is eliminated. Stable conditions are established in the region of the heated sample so that the thermal decomposition, whether or not in the presence of a reactant, proceeds in controlled fashion.

Within the thermogravimetric chamber the support mechanism joined to the sample holder is encompassed by a baffle having a mixing chamber partially in the hot zone adjacent the sample and partially in an adjacent heated zone. The mixing chamber has separate gas flow paths on the side away from the sample, adjacent an outlet for the thermogravimetric chamber. A purge gas flow path leads into the mixing chamber via a separate transition chamber partially within the heated zone which also encompasses a portion of the support mechanism and is in communication with a first flow path into the mixing chamber. The reactant flow, and any entrained effluent, move in the opposite direction past the sample toward the mixing chamber. These gases enter an open end of the mixing chamber adjacent the sample, and mixing occurs in the hot zone because the purge gases are carried into proximity with the open end. As mixing occurs the gases leave the mixing chamber via the second flow path and are directed outside the system through the adjacent thermogravimetric chamber outlet. The flows are balanced in such manner that the purge gas which shields the support mechanism does not pass entirely through the mixing chamber into the region of the sample, and the net gas flow provides constant force on the sample. The products of decomposition are diluted but remain at high temperature in the heated zone until they reach the outlet region. Thus condensation on the support mechanism and thermogravimetric chamber does not occur.

In a specific example of a system in accordance with the invention, for instrumentation, a sample is suspended from a precision balance by a hang-down wire within a thermogravimetric chamber tube extending vertically through a furnace. The balance is disposed within a balance chamber filled with a purge gas (e.g. helium) that flows down along the hang-down wire. A flow outlet from the thermogravimetric chamber is disposed above the furnace within a hood that provides a degree of thermal isolation and defines the heated zone. Within the thermogravimetric chamber, an upper baffle assembly about the hang-down wire comprises a conduit system of varying diameter including an upper transition chamber extending adjacent or partially within the heated zone, and a central conduit leading from the lower end of the transition chamber to the upper end of the mixing chamber, the lower part of which is in the hot zone of the furnace. An interior tube collinear with the central conduit extends down into the interior of the mixing chamber to a region in the hot zone above a bottom opening in the mixing chamber, just above the sample. Purge gases flowing down the hang-down wire of the central conduit of the upper baffle also pass outside the upper baffle in the space between the upper baffle and the inner wall of the thermogravimetric chamber. The initially cool purge gases moving within the upper baffle toward the mixing chamber protect the hang-down wire from products of decomposition. Both the upwardly flowing reactant and gases of decomposition enter the mixing chamber from the opposite side and mix with the purge gas in the hot zone, without the purge gas reaching the sample. The mixed flow passes upwardly about the central tube to a second flow path through perforations in the upper surface of the mixing chamber, to the outlet orifice in the heated zone within the hood. With this configuration, the only gases contacting the hang-down wire and suspension mechanism for the sample holder are the purge gas in the cool region of the upper chamber, and the mixed effluent and reactant at high temperature in the hot zone, so that no deposition of condensing matter on the hangdown wire can take place. Furthermore, flows are balanced such that the transition region within the mixing chamber is stable and the gas composition in the region of the sample is constant.

The system is further augmented by an inlet feed below the thermogravimetric chamber, by which a reactant gas may be passed in the chamber, and a lower baffle extending up from the lower end of the furnace to adjacent but just below the sample holder. The lower baffle confines the reactant gas flows to the space adjacent the inner periphery of the thermogravimetric chamber, exposing the gases to the interior heat of the furnace and preheating them more efficiently while still providing access of the gases to the region of the sample and sample holder. The lower baffle may be configured in various ways, so that a temperature sensor may be mounted adjacent but below the sample holder, at the same level as the sample, or be sealed within the lower baffle, to enable accurate temperature readings to be taken under different conditions.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
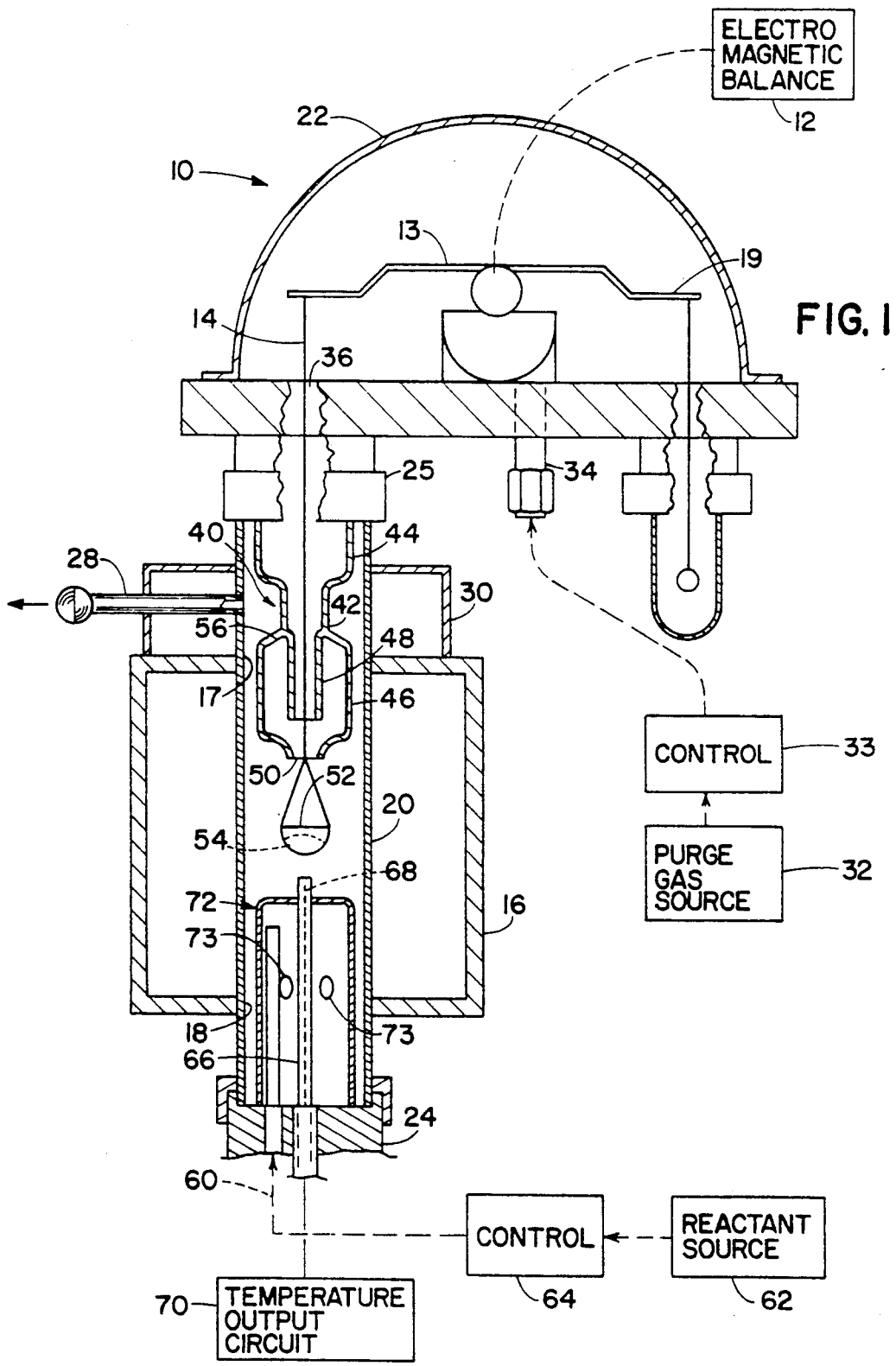
FIG. 1 is a generalized block diagram and schematic representation of a system in accordance with the invention.

A thermogravimetric instrument 10 in accordance with the invention is shown as it is used in conjunction with a precision electromagnetic balance 12 having an arm 13 from which a hang-down wire 14 depends into the interior of a furnace 16 having upper and lower orifices 17, 18. Opposite the arm 13 is a counterbalance arm and tare weight device 19 to compensate for the weight of the arm 13, hang-down wire 14 and sample holder. Extending through the furnace 16 and encompassing the hang-down wire 14 is a thermogravimetric chamber 20, including a hollow glass cylinder, which extends between a sealed balance chamber 22 at its upper end, and an end seal 24 at its lower end. The balance chamber 22 encompasses the balance 12, arm 13 and device 19 and is a chamber for a purge gas. An upper end seal structure 25 couples the upper end of the thermogravimetric chamber 20 to the balance chamber 22, in hermetically sealed fashion. Near the upper end of the thermogravimetric chamber 20 an outlet tube 28 above the furnace 16 extends radially outward within a heat retaining hood 30 that also encompasses the upper end of the thermogravimetric chamber 20. The heat retaining hood 30 defines a heated zone because conduction and connection from the hot zone within the furnace 16 develops a substantial although lower temperature level under the hood 30.

Figure 2:
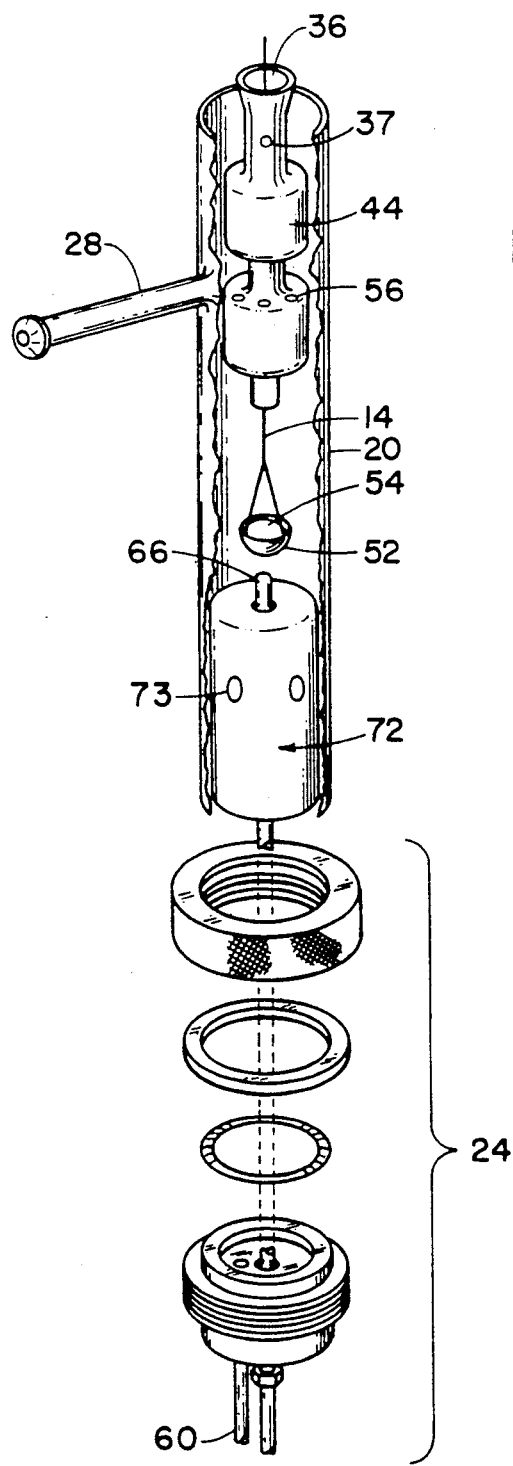
FIG. 2 is an exploded perspective view of portions of the system of FIG. 1 in accordance with the invention.

In the system of FIGS. 1 and 2, a precision electromagnetic balance 12 is depicted within the balance chamber 22, but any suitable form of precision mass measurement system capable of measuring minute changes in mass in a dynamic fashion is suitable. A purge gas source 32 feeds an inert gas, such as helium, through an adjustable control 33 to a purge gas inlet 34 into the balance chamber 22. An opening 36 from the balance chamber 22 communicates with the interior of the thermogravimetric chamber 20, feeding the purge gas into the interior of an upper baffle 40 having an intermediate central conduit 42 concentric with and spaced apart from the hang-down wire 14. Gases entering at the opening 36 also pass outwardly via radial holes 37 near the upper end of the baffle 40, to flow down the gap between the baffle 40 and the inner wall of the thermogravimetric chamber 20, thus preventing backstreaming of gases and products of decomposition from within lower regions of the chamber 20.

Figure 3:
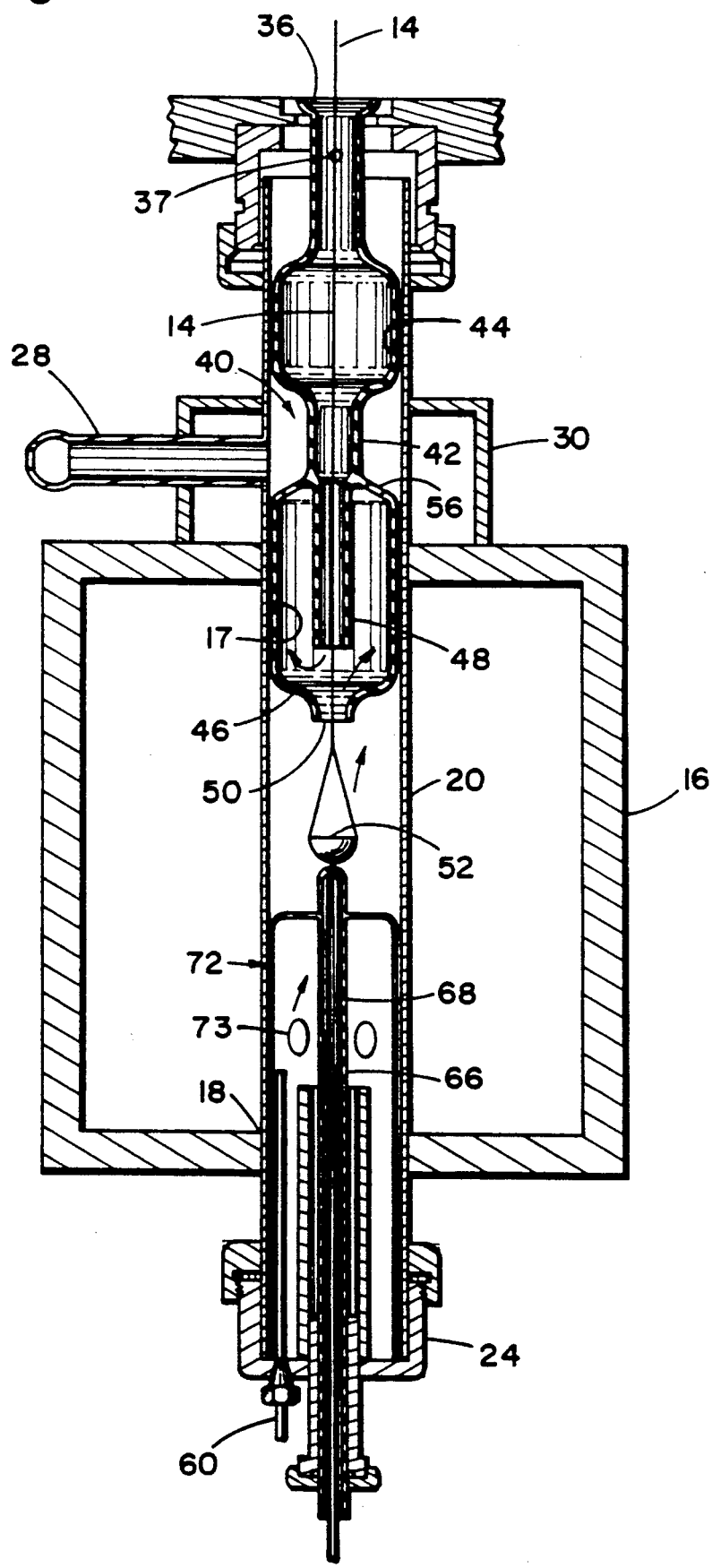
FIG. 3 is a cross-sectional view of the system of FIGS. 1 and 2, showing further details thereof.

As best seen in FIGS. 1 and 3, the upper baffle 40 includes a pair of spaced apart chambers 44, 46 of larger cross-section than an intercoupling central conduit 42. The uppermost of these chambers constitutes a transition chamber 44 outside the hot zone of the furnace 16 and thermogravimetric chamber 20 but extending close to or within the heated zone and the hood 30. The second chamber, the lower end of which extends into the hot zone, may be called a mixing chamber 46. In the interior of the mixing chamber 46, a smaller interior tube 48 (FIGS. 1 and 3) extends down from the central conduit 42 concentrically about the hang-down wire 14 into the hot zone, close to but spaced apart from the lower end of the mixing chamber 46. A bottom orifice 50 at the lower end of the mixing chamber 46 is open to the interior of the thermogravimetric chamber 20, and proximate a sample holder 52 on which a sample 54 is disposed for analysis. The mixing chamber 46 is disposed, in this example, so that its mid-region lies approximately at the upper wall of the furnace 16, with the lower end of the interior tube 48 and the bottom orifice 50 both in the hot zone of the furnace 16. The upper end of the mixing chamber 46 is within the adjacent heated zone maintained within the hood 30.

A first pathway for gases into the mixing chamber 46 is via transition chamber 44, the central conduit 42 and interior tube 48. The mixing chamber 46 also has flow openings 56 in its upper surface, radially spaced from the central conduit 42, providing a second flow pathway about the central conduit 42, and into the region of the outlet tube 28 that extends from the chamber 20.

At the lower end of the thermogravimetric chamber 20, the lower end seal structure 24 has an inlet port for a reactant gas line 60, the reactant gas being fed from a supply 62 via an adjustable control 64. A hollow shield tube 66 disposed along the central axis of the chamber 20 encloses (as best seen in FIGS. 2 and 3) a temperature sensor 68 extending through the center of the lower end seal 24 into the interior of the thermogravimetric chamber 20, to a level just below the sample holder 52. An output circuit 70 is in electrical circuit with the temperature sensor 68 to indicate or transmit to associated units (not shown) the temperature level within the chamber 20 in the vicinity of the sample 54.

A lower baffle 72 in the form of a cylinder is disposed in the lower end of the thermogravimetric chamber 20, below the sample 52, and concentrically about the shield tube 66. The lower baffle 72 is of cylindrical outline and includes side openings 73 in this example to provide a restricted flow path around the outside of the lower baffle 72 within the thermogravimetric chamber 20. Thus reactant gas from the supply 62 is passed outside the lower baffle 72, into the hot zone within the furnace 16 and into intimate contact with the heated walls of the thermogravimetric chamber 20, before entering the region of the sample holder 52 and sample 54.

In the operation of the system of FIGS. 1-3, the thermogravimetric chamber 20 is fed from below with a reactant gas from the supply 62, while purge gas from the source 32 is fed from the balance chamber 22, into the central conduit 42 in the upper baffle 40, and downwardly through the transition chamber 44 central conduit 42 and interior tube 48 into the mixing chamber 46. The furnace 16 is then heated to the fixed or variable temperature level needed for decomposition of the sample 54, usually in the presence of a reactant gas. This temperature may be adjusted in accordance with the level sensed by the output circuit 70. The reactant gas can be air, or some other suitable medium, even as corrosive as HCL, $SO_2$, HF or ammonia. If a corrosive reactant is used the contacted surfaces should be of materials that are substantially unaffected by it. The reactant can be the vapor of a liquid, or a catalyst may be incorporated in the sample that initiates and maintains the needed reaction. The reactant flow is established in a particular balance, as described hereafter, relative to the oppositely directed flow of purge gas moving downwardly through the upper baffle 40. The effluent flows from decomposition of the sample 54 entrained in the reactant flows, are stabilized by this balance and because the lower baffle 72 assures uniform preheating of the reactant gas. Thus under steady state conditions temperature levels remain substantially the same.

The oppositely directed purge gas first enters the transition chamber 44, outside the hood 30. The downward flow of pure purge gas encompasses the hangdown wire 14 and the outside of the baffle 40, and insures that in this region the products of decomposition cannot recondense on the wire 14 because they cannot overcome the downward flow to leave the heated zone. Furthermore, as the purge gas continues to flow downwardly within the upper baffle 40, it enters the narrowed central conduit 42 region and then the further narrowed interior tube 48 which leads into the lower region of the mixing chamber 46, within the hot zone of the chamber 20. As the purge gas passes through these diminishing cross-sectional areas its velocity may increase somewhat but the flow rate is sufficient in any event to prevent counterflow of gases from the opposite direction. The reactant gas and effluent from the sample 54 enter the mixing chamber 46 via the bottom orifice 50 to encounter and be mixed with the descending purge gases in this limited volume. Because the temperature is substantially that of the hot zone, and because the flow pressure of reactant is kept slightly greater than that of the lighter purge gas, the gases mix within the chamber 46, outside the interior tube 48. They then pass upwardly through the outer flow openings 56 in the mixing chamber 46 to the heated zone within the hood 30, and move through the outlet tube 28 from the system, without condensing on the interior wall of the thermogravimetric chamber 20, or upon the outer surfaces of the upper baffle 40.

Thus it may be seen that the downward and upward flows are maintained in approximate equilibrium, but with a net flow being established in the upward direction away from the sample 54. This gas movement introduces a slight upward force on the sample holder 52, but by stabilizing forces prior to the initiation of the reaction, accurate readings may be taken at all times.

It can be seen that the sample 54 in the chamber 20 is isolated not only from transient and variable gas flows but from the effects of temperature change. The positive flow of purge gas is so confined and controlled that the gases cannot flow back into the balance chamber 22. Since condensation by the volatile decomposition products is minimized and since backstreaming of reactant gas into the region of the balance chamber 22 is prevented, this system can be used for studying large, fume-generating samples. Because there is virtually no gas mixing at the sample, products evolved during the reaction do not destabilize the readings. The system can be readily set up for different modes and samples, because the assembly of baffles and thermogravimetric chamber permits changes to be made quite readily for initiation of different runs.

It will be appreciated that the conditions of operation, including the size and flow rates of the gases, the size and character of the sample and other aspects of the geometry can necessitate routine adjustments and balances of the conditions for a particular thermogravimetric study. The following is one example of a practical operation:

A. A 10 ml sample holder 52 is placed on the hangdown wire 14 and the balance is tared to 0.000 mg with no gas flow.

B. Without a flow of reactant, and with the outlet tube 28 open, helium is purged through the balance chamber 22 at about 500 ml/min, to remove all air from the balance chamber 22 in expeditious fashion.

C. The reactant line 60 is opened and air is flowed into the thermogravimetric chamber 20 to flow upwardly at a rate of between 10 and 100 ml/min, this flow being adjusted until a steady state is achieved in which the balance reads approximately −14 mg, with a fluctuation of less than ±0.01 mg.

D. The helium purge rate is then reduced to about 50 ml/min.

E. The helium purge is then stopped and the air flow is adjusted to the desired flow rate (specifically in one practical example 100 ml/min). The reading of the balance 12 is taken when the flow rate is stabilized, and represents the buoyancy force of the air flow on the sample holder 52.

F. The helium purge is then turned on again, and established at a suitable level to achieve positive gas separation within the mixing-separating chamber 46.

Systems in accordance with the invention have been used in a number of thermogravimetric measurements that have heretofore presented specific problems. For example, determining the ash content of 1 g of polyethylene has presented significant difficulties because melting and boiling out of the sample and subsequent thermal decomposition resulting in dense fumes would deposit sticky or tar-like material over the inside of the chamber and the hang-down wire. This would then adversely affect the accuracy of the run, and moreover require a massive cleanup. Using the system in accordance with the invention, however, and applying the desired heating profile, no contamination occurred and there was no condensation on the hang-down wire. Repeated runs enable the determination that the ash content in the polyethylene was 0.047% with a precision of ±0.002%.

As another example, fluorinated polyvinylchloride (PVC) evolves hydrochloric and hydrofluoric gases in thermal deposition. These are extremely corrosive at the high temperatures applied, and further tar depositions contaminate the balance system. This renders an evolved gas analysis (EGA) extremely difficult to achieve. Using a device in accordance with the invention, with suitable incorporation of corrosion-resistant materials, there was no contamination and any corrosion effects were undetectable. Reading accuracies of ±0.01% of mineral filler were readily obtained.

Figure 4:
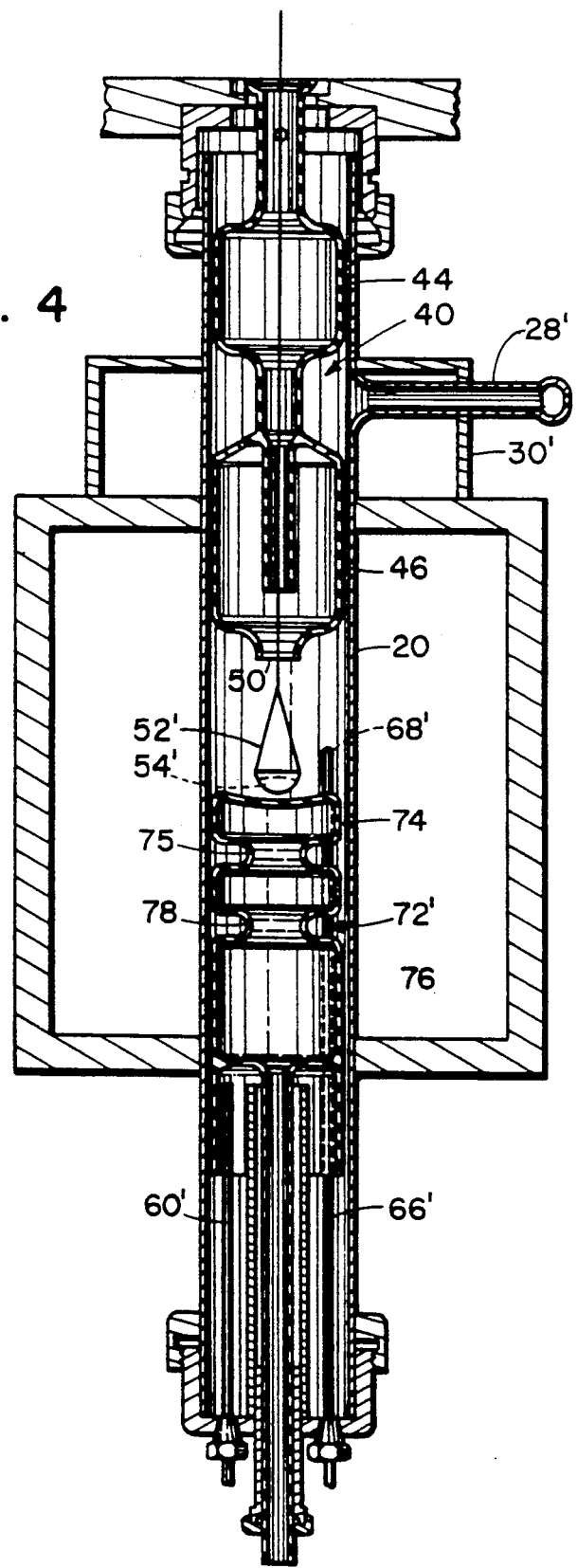
FIG. 4 is a cross-sectional view of a different example of a system in accordance with the invention in which the temperature sensor is adjacent the sample at the same levels.

In a somewhat different arrangement in accordance with the invention, as shown in FIG. 4, the temperature sensor is disposed along one wall of the thermogravimetric chamber 20 and the shield tube 66' and internal temperature sensor 68' are mounted along the inner periphery of the chamber 20, at substantially the level of the sample holder 52'. The lower baffle 72' has a pair of sections..of larger diameter 74, 75, 76 and also intervening sections 77, 78 of smaller diameter. The larger diameter sections are spaced apart from the inner surface of the chamber 20, and the lower baffle 72, has a central conduit extending outside the lower end of the furnace 16 and mounted in the lower end seal 24. The upper end of the lower baffle 72' extends well into the hot zone, into the proximity of the sample holder 52', so that flowing gases from the reactant conduit pass within a lower pocket, then move outside and upwardly of the lower baffle 72', having excellent thermal contact with the hot walls of the thermogravimetric chamber 20 in the hot zone of the furnace 16, until they reach the region about the sample 54'.

This arrangement enables the temperature sensor 68' to be positioned at the level of the sample 54' itself for greater accuracy, particularly where a sample is large and a temperature difference might therefore exist.

Figure 5:
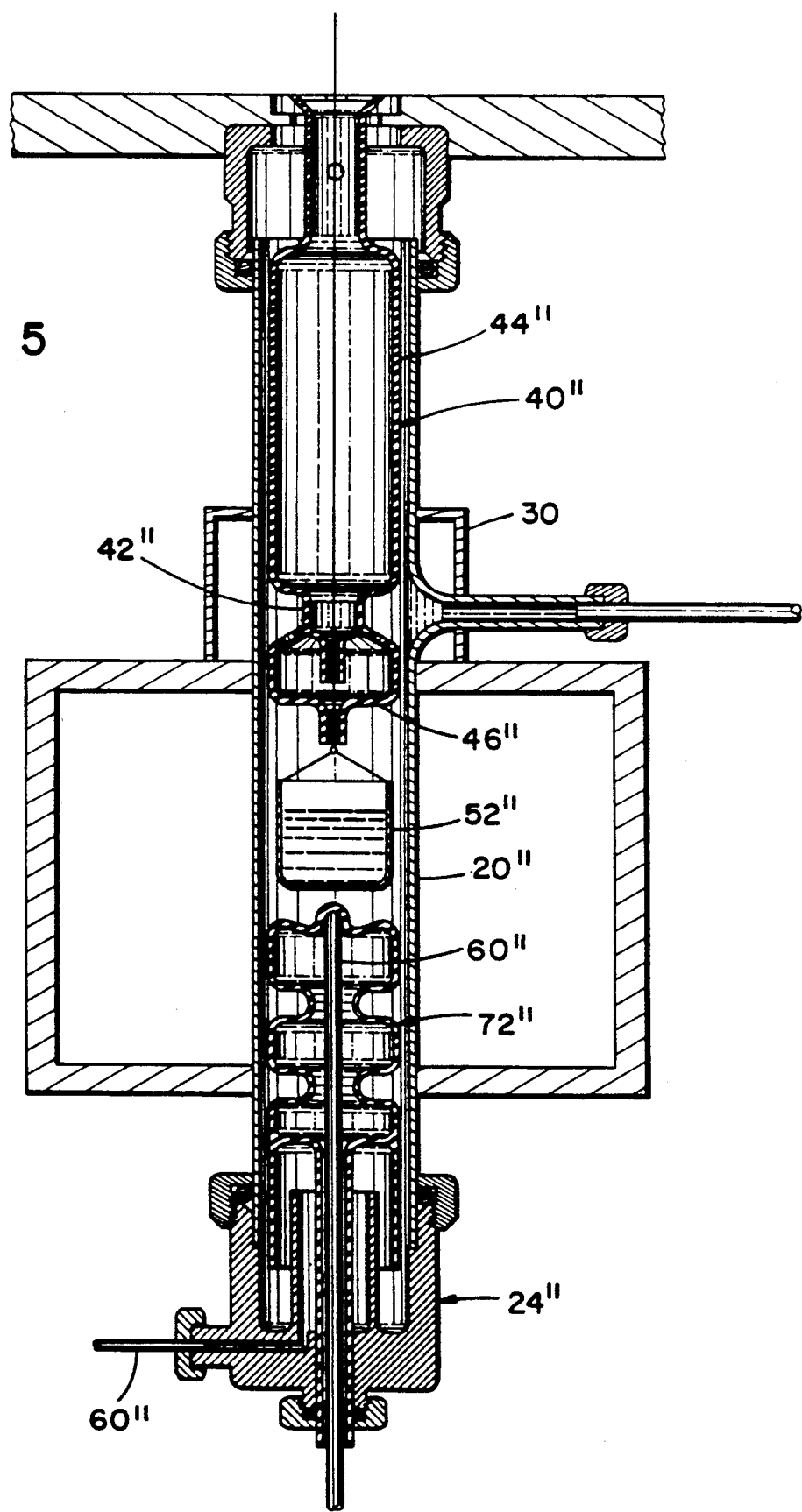
FIG. 5 is a cross-sectional view of yet another example in which the transition chamber is extended and the temperature sensor is isolated from internal gases.

In another example, as seen in FIG. 5, the transition chamber 44" is of extended length, and the mixing chamber 46" is relatively shorter. The lower end of the transition chamber 72" is within the heated zone, and the central region of the mixing chamber 46" is midway between the hot zone and the heated zone. This arrangement improves gas flow stability for many applications.

At the lower baffle 72", the reactant inlet line 60" is coupled into a sidewall of the lower end fitting 24" and internal walls establish a reentrant path before the reactant moves upwardly through the gap between the outer baffle 72" wall and inner chamber 20" wall. The temperature sensor shield 66" is completely contained within the lower baffle 72", mating with a topmost projection 80 on the lower baffle 72", just under the sample holder 52". With this arrangement the temperature sensor is completely protected from corrosive gases that might be encountered or used.

Although various forms and modifications in accordance with the invention have been shown or described, it will be appreciated that the invention is not limited thereto but encompasses all modifications and expedients within the scope of the appended claims.

What is claimed had desired to be secured by letters patent is as follows:

1. An apparatus for measurement of changes in mass of a decomposing sample and an outlet outside the hot zone comprising:

a sample holder in a thermogravimetric chamber having a hot zone and an outlet outside the hot zone, wherein the sample holder supports a decomposing sample a mass measuring system adjacent one side of the chamber and including sample support means within the hot zone of the thermogravimetric chamber and including coupling means between the sample support means and the mass measuring system;

means for feeding a reactant gas into the thermogravimetric chamber toward the sample from a side opposite the sample from the mass measuring system;

mixing chamber means encompassing at least a portion of the coupling means and disposed to extend into the hot zone of the thermogravimetric chamber adjacent the sample, the mixing chamber means including aperture means open to the sample and aperture means in communication with the thermogravimetric chamber outlet; and means for feeding purge gas into the mixing chamber means from the mass measuring system side into the hot zone at a rate selected relative to the flow of the reactant gas to maintain hot reactant gas in the region of the sample.

2. The invention as set forth in claim 1, further including, in the path of the purge gas, a transition chamber outside the hot zone of the thermogravimetric chamber and a central gas flow means between the transition chamber to within the mixing chamber means adjacent but spaced apart from the aperture means.

3. The invention as set forth in claim 2, further including reactant gas flow control means disposed on the opposite side of the sample from the mixing chamber means within the thermogravimetric chamber to direct the reactant gas flow toward the inner wall of the thermogravimetric chamber.

4. The invention as set forth in claim 3 above, wherein the thermogravimetric chamber is vertically disposed, wherein the transition chamber, central gas flow means and mixing chamber means comprise an upper baffle and the reactant gas flow control means comprises a lower baffle.

5. The invention as set forth in claim 4 above, wherein the thermogravimetric chamber is cylindrical about a central axis and wherein the upper and lower baffles have outer peripheries concentric with the thermogravimetric cylinder.

6. The invention as set forth in claim 5 above, wherein the transition chamber and mixing chamber means comprises an upper baffle including a central conduit about the sample support means between the transition chamber and mixing chamber means, an internal tube about a portion of the sample support means in communication with the central conduit means and of smaller cross-sectional area, and having an open end within the hot zone of the mixing chamber means, the mixing chamber means further including outlet aperture means on the upper side thereof radially separated from the central conduit means, the thermogravimetric chamber outlet being disposed in the region of the central conduit means.

7. The invention as set forth in claim 6 above, further including means for controlling the flow rates of the reactant gas and the purge gas such that the purge gas flows through the central portion of the upper baffle to the outlet end of the inner tube, and the reactant gas and products of decomposition enter the mixing chamber means at the aperture means therein, and the purge gas, reactant gas and products of decomposition exit the mixing chamber means via the outlet aperture means therein.

8. The invention as set forth in claim 7 above, wherein the apparatus further includes furnace means encompassing a portion of the thermogravimetric chamber to establish the hot zone, hood means providing a thermal insulation chamber about the outlet means to establish an external zone heated by the furnace means, and upper and lower end seal means coupled to the thermogravimetric chamber.

9. The invention as set forth in claim 1 above, further including temperature sensing means disposed in the thermogravimetric chamber in the region of the sample.

10. The invention as set forth in claim 9 above, wherein the temperature sensing means is disposed at the level of the sample.

11. The invention as set forth in claim 10 above, wherein the system further comprises a lower baffle having a hollow interior and the temperature sensing means is disposed within the lower baffle with an end in proximity to the sample.

* * * * *

UNITED STATES PATENT AND TRADEMARK OFFICE
CERTIFICATE OF CORRECTION

PATENT NO. : 5,055,264
DATED : October 8, 1991
INVENTOR(S) : Jerzy P. Czarnecki

It is certified that error appears in the above-identified patent and that said Letters Patent is hereby corrected as shown below:

Column 7, line 36, delete ".." after the word "sections.

Column 7, line 39, "72," should read --72'--.

Column 8, line 18, insert --;-- after the word "sample".

Signed and Sealed this

Twentieth Day of April, 1993

Attest:

MICHAEL K. KIRK

Attesting Officer

Acting Commissioner of Patents and Trademarks